(12) United States Patent
Heritier et al.

(10) Patent No.: US 6,576,719 B2
(45) Date of Patent: Jun. 10, 2003

(54) ISOBUTENE POLYMERIZATION PROCESS

(75) Inventors: Jacques Heritier, Sausset-les-Pins (FR); Alain Pinede, Ventabren (FR); Christian Sait, Cornillon-Confoux (FR)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/942,970

(22) Filed: Aug. 31, 2001

(65) Prior Publication Data

US 2002/0026024 A1 Feb. 28, 2002

Related U.S. Application Data

(63) Continuation of application No. PCT/GB00/00869, filed on Mar. 9, 2000.

(30) Foreign Application Priority Data

Mar. 12, 1999 (FR) .............................. 99 03267

(51) Int. Cl.$^7$ .............................. C08F 2/00; C08F 10/10
(52) U.S. Cl. .............................. 526/60; 526/59; 526/61; 526/348.7; 585/501
(58) Field of Search .................. 526/59, 61, 348.7, 526/60; 585/501

(56) References Cited

U.S. PATENT DOCUMENTS 4,620,049 A   10/1986   Schmidt et al.
5,155,184 A * 10/1992   Laurent et al. .............. 526/59

FOREIGN PATENT DOCUMENTS

| EP | 0 099 131 | 1/1984 |
|---|---|---|
| EP | 0 398 706 A2 | 11/1990 |
| FR | 2 625 506 | 7/1989 |
| FR | 2 749 014 | 11/1997 |
| WO | 96/41822 | 12/1996 |

* cited by examiner

Primary Examiner—Fred Teskin
(74) Attorney, Agent, or Firm—Nixon & Vanderhye

(57) ABSTRACT

The present application relates to a process for the continuous polymerization of isobutene while maintaining at a constant desired value a property P (viscosity or average molecular mass) of the polymer produced. The polymerization is conducted in a reactor comprising a boiling liquid reaction phase which contains the monomer and the polymer being formed, in equilibrium with a gas phase on top of the said liquid phase, by continuous introduction into the reactor of a catalyst and of a C4 hydrocarbon feed mixture comprising the monomer, and by continuous withdrawal from the reactor of the liquid reaction phase, which is subsequently subjected continuously to at least one purification step which is intended to isolate the polyisobutene produced. The process comprises the determination of a target value V of the partial pressure piC4 of the isobutene in the gas phase of the reactor corresponding to the property P, by virtue of an empirical relationship established beforehand between the property P of the polyisobutene produced and piC4. During the polymerization, piC4 is measured and held constant at around the target value V by acting on the flow rate Qc of the catalyst introduced into the reactor and/or on the flow rate Qh of the C4 hydrocarbon feed mixture.

13 Claims, 5 Drawing Sheets

ISOBUTENE POLYMERIZATION PROCESS

This is a continuation of application No. PCT/GB00/00869, filed Mar. 9, 2000.

The present invention relates to a process which makes it possible to control the viscosity or the average molecular mass of a polyisobutene produced continuously in a reactor in liquid phase.

BACKGROUND OF THE INVENTION

It is known to polymerize isobutene continuously in a reactor comprising a boiling liquid reaction phase containing the monomer and the polymer being formed, above which there is a gas phase comprising, in particular, the monomer which is in equilibrium with the liquid phase. The continuous polymerization is brought about in particular by continuous feeds into the reactor of the monomer and of a catalyst and by continuous withdrawal from the reactor of the liquid phase, which is, generally, subjected subsequently to one or more purification steps which are intended to isolate the polyisobutene produced.

The monomer often consists of isobutene, originating from a mixture of butenes and/or butanes.

In general, the polymerization reaction is conducted continuously with the aid of a catalyst of cationic type and, if appropriate, of a cocatalyst.

In a continuous polymerization, the monomer, i.e. isobutene, is generally supplied by means of an essentially C4 hydrocarbon cut, that is to say, a mixture comprising isobutene, other C4 olefins and/or C3 to C7 alkanes, especially C4 alkanes. The quality of the monomer supply may vary over time, such that it adversely affects the polymerization conditions and, consequently, the quality of the polymer obtained.

The applications of polyisobutenes are often linked to their rheological properties. One of the essential characteristics of polyisobutene is its viscosity or its average molecular mass.

In a continuous polyisobutene production process, the average residence time of the polymer in the polymerization reactor can be relatively long. Moreover, the reaction mixture withdrawn continuously from the polymerization reactor enters one or more polymer purification steps. The final polymer is therefore isolated and purified after an additional time which may generally be a number of hours, for example from 3 to 12 hours, such that any analysis of the polymer at the end of this last step is carried out very late. Consequently, the time elapsed between a deviation measurable from the analysis of the viscosity or of the average molecular mass of the polyisobutene, and the correction of the said deviation in the polymerization reactor, is relatively great. This type of deviation therefore gives rise to the production of product which is outside the specifications of viscosity or average molecular mass, generally in a not inconsiderable amount.

Methods have been investigated in the past to solve the above mentioned problem.

In the process of the French Patent Application 2 625 506, a method is disclosed to determine one or more polymer properties using a correlative relation with absorption measurements carried out on the polymer with an infrared spectrophotometer. A process control using this method is also disclosed but it does not address the problem solved by the present invention.

The U.S. Pat. No. 4,620,049 describes a method adapted for controlling the molecular weight of a product output from a polybutene reactor. The method in particular comprises determining a formula correlating molecular weight simultaneously with temperature of the reactor and concentration of isobutene in the reactor. The desired product molecular weight is then obtained by altering, through the use of the formula, the temperature of the reactor and/or the concentration of isobutene in the reactor. However the principle of this method does not comprise maintaining constant the partial pressure of the isobutene in the gas phase of the reactor, in particular independently of the polymerization temperature. Moreover, involving the temperature of the reactor in the formula of this method implies that the temperature may vary even slightly and therefore affects the quality of polyisobutene produced, such as the unsaturated termination content of the polymer.

SUMMARY OF THE INVENTION

The present invention describes a process control which makes it possible to correct the fluctuations in the viscosity or in the average molecular mass of the polyisobutene and, therefore, to intervene more rapidly in the conditions of the polymerization in the reactor in order to limit the amount of polyisobutene which is produced outside the specifications.

The present invention relates to a process for maintaining a property P of a polyisobutene at a constant desired value in the course of an isobutene polymerization conducted continuously in a reactor comprising a boiling liquid reaction phase which contains the monomer and the polymer being formed and is in equilibrium with a gas phase on top of the said liquid phase, the polymerization being conducted by continuous introduction into the reactor of a catalyst and of a C4 hydrocarbon feed mixture comprising the monomer, and by continuous withdrawal from the reactor of the liquid reaction phase, which is subsequently subjected continuously to at least one purification step which is intended to isolate the polyisobutene produced, this process being characterized in that the property P is selected from the viscosity and the average molecular mass of the polyisobutene produced and in that, by virtue of an empirical relationship established beforehand between the property P of the polyisobutene produced and the partial pressure piC4 of the isobutene in the gas phase of the reactor, a target value V is determined for piC4, corresponding to the desired value of the property P, and in that, during the polymerization, the partial pressure piC4 in the gas phase of the reactor is measured and the said partial pressure piC4 is held constant at around the said target value V by acting on the flow rate Qc of the catalyst introduced into the reactor and/or on the flow rate Qh of the C4 hydrocarbon feed mixture.

DETAILED DESCRIPTION OF PREFERRED EMBODIMENTS

Figure 1:
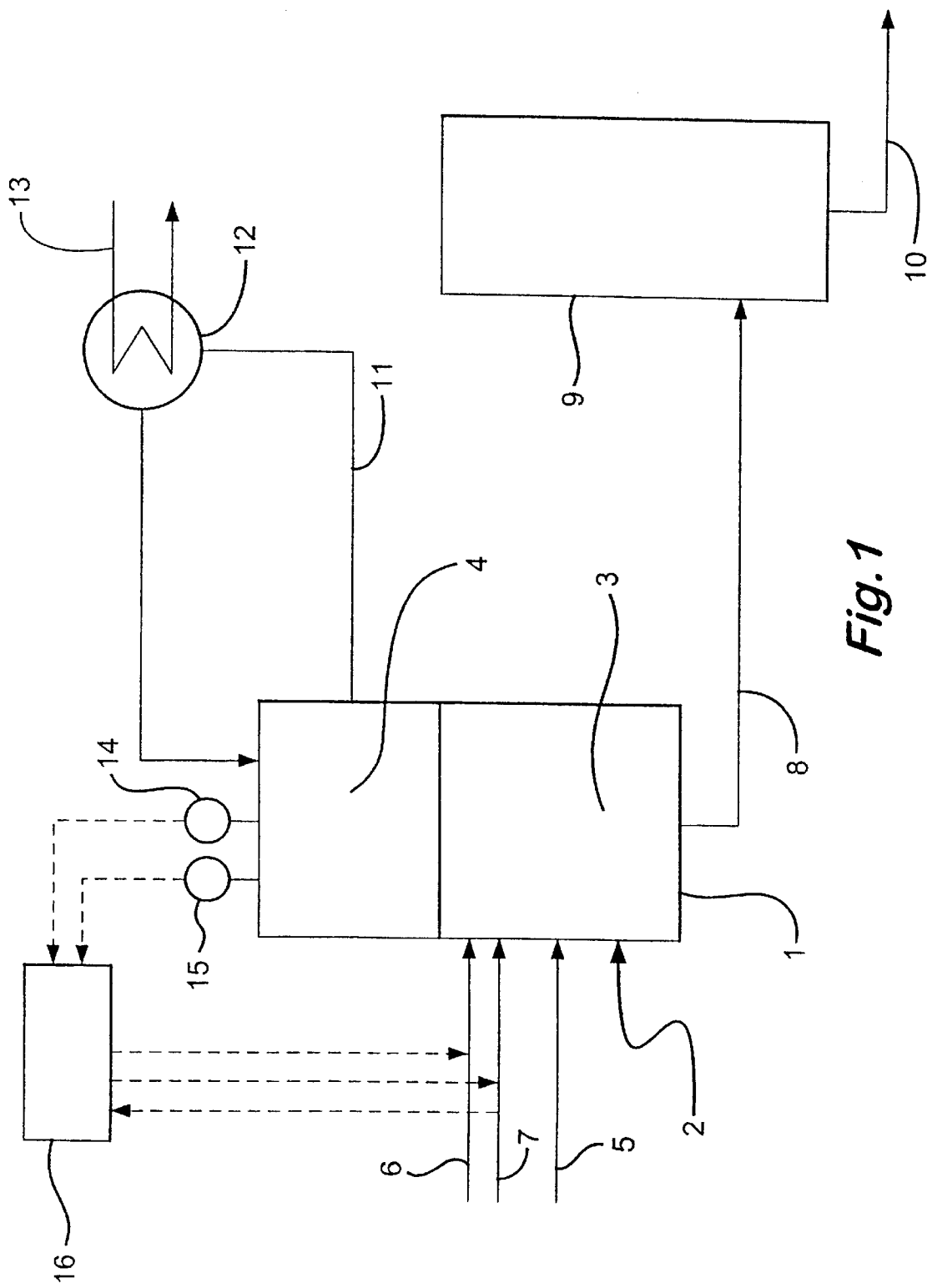
FIG. 1 shows, diagrammatically, an example of an apparatus for continuous production of the polyisobutene

It has been found surprisingly that the partial pressure piC4 of the isobutene in the gas phase of the reactor is considered as an essential and critical parameter in the control of the quality of the continuously produced polyisobutene, especially with regard to the viscosity or average molecular mass of the polymer.

By property P is meant, generally, the viscosity or average molecular mass measured on the polyisobutene, especially after withdrawal of the liquid reaction phase from the reactor, and in particular after at least one step of purification intended to isolate the polymer produced.

According to one aspect of the present invention, the property P which will be held at a constant desired value during the polymerization can be any viscosity of the polyisobutene, selected, for example, from the kinematic viscosity, the dynamic viscosity, the specific viscosity, the reduced viscosity and the intrinsic viscosity. It is possible to measure the kinematic viscosity, i.e. the rate of flow of the polymer in a capillary tube, using, for example, the standardized method ASTM D445. It is also possible to measure the dynamic viscosity, which is linked to the kinematic viscosity by a relationship involving the density of the polymer, using, for example, a viscometer whose principle consists in measuring a pressure drop at a certain temperature and in calculating the viscosity from, for example, the Hagan-Poiseuille equation. More particularly, it is possible to use a viscometer under the trade name VISCOMATIC® produced by the company FLUIDYSTEME. It is also possible to measure the intrinsic viscosity in a solvent, for example cyclohexane, at a given temperature, for example 30° C.

The viscosity of the polyisobutene produced can also be measured by infrared or near-infrared spectrophotometry, such as is disclosed in French Patent Application No. 2 625 506.

The constant desired value of the viscosity of the polyisobutene produced can be that corresponding to.
(i) a kinematic viscosity, measured at 100° C., of from 5 to 50,000 centiStocks (cSt), preferably from 10 to 40,000 cSt, or
(ii) a dynamic viscosity, measured at 100° C., of from 4 to 45,000 centipoise (cP) preferably from 8 to 36,000 cP, or
(iii) an intrinsic viscosity, calculated from the measurements of the specific viscosity of the polyisobutene in solution in cyclohexane at 30° C., of from 1 to 25 dl/g, preferably from 2 to 20 dl/g According to another aspect of the present invention, the property P which will be maintained at a constant desired value during the polymerization can be the average molecular mass of the polyisobutene produced. By average molecular mass is meant any average molecular mass of the polyisobutene, for example the number-average molecular mass Mn or weight-average molecular mass Mw; which are generally measured by gel permeation chromatography, a method which is often known under the name of size exclusion chromatography, or else the viscometric average molecular mass Mv. The average molecular mass of the polyisobutene produced can be measured by infrared or near-infrared spectrophotometry, such as is disclosed in French Patent Application No. 2 625 506.

The constant desired value of the average molecular mass of the polyisobutene produced can be that corresponding to:
(i) a number-average molecular mass, Mn, of from 300 to 6700 daltons, preferably from 400 to 6000 daltons, or
(ii) a weight-average molecular mass, Mw, of from 400 to 20,000 daltons, preferably from 600 to 18,000 daltons, or
(iii) a viscometric average molecular mass, Mv, of from 380 to 16,900 dl/g, preferably from 500 to 15,000 dl/g.

In the present invention, the polyisobutene can be an isobutene homopolymer or, more generally, a copolymer of isobutene with at least one other C4 olefin in a proportion of less than 30%, preferably of less than 25%, by weight, for example from 0.1 to 25% by weight. Generally speaking, high molecular weight polyisobutenes contain essentially isobutene. Low-viscosity polyisobutenes may comprise more 1-butene and/or 2-butene comonomers than high molecular weight polyisobutenes.

Thus, in the process of the present invention, the monomer consists of isobutene and the optional comonomers of 1-butene and cis- and trans-2-butene. The polymerization is conducted by continuous introduction into the reactor of a C4 hydrocarbon feed mixture comprising the monomer with generally at least one other C4 olefin and/or at least one C3 to C7 (cyclo)alkane, in particular a C4 alkane. Such a mixture may comprise by weight from 0 to 40%, preferably from 0 to 30%, of 1-butene, from 0 to 20%, preferably from 0 to 15%, of cis-2-butene, from 0 to 40%, preferably from 0 to 30%, of trans-2-butene, from 0 to 50%, preferably from 0 to 40%, of one or more C3 to C7 (cyclo)alkanes, such as butane or isobutane, and from 5 to less than 100%, preferably from 10 to less than 50%, of isobutene.

The C4 hydrocarbon feed mixture can be introduced directly into the boiling liquid reaction phase. It can also be introduced indirectly into the boiling liquid reaction phase by addition to any other liquid introduced into the reactor, for example to a liquid obtained by cooling and condensation of condensable gas of the gas phase which escapes from the top part of the reactor and is returned into the reactor. The C4 hydrocarbon feed mixture can also be introduced in its entirety into the gas phase as a spraying liquid hydrocarbon, as disclosed in French Patent Application No. 2 749 014.

The boiling liquid reaction phase generally contains isobutene and one or more other C4 olefins and/or one or more C3 to C7 (cyclo)alkanes, the polymer being formed, the catalyst and, if appropriate, a cocatalyst.

The boiling liquid reaction phase can be agitated by any known means, in particular with the aid of a mechanical stirrer. The boiling liquid reaction phase can also be agitated by forced circulation of this medium, which can include the withdrawal and the reintroduction into the reactor of a portion of the boiling liquid reaction phase, in particular with the aid of a so-called recycling pump The boiling liquid reaction phase has above it a gas phase, especially a condensable gas phase. Consequently, a condensable gas can escape from the top part of the reactor containing the gas phase. In general, this gas is condensed outside the reactor in order, in particular, to remove the heat of the polymerization reaction. After cooling and condensation of this gas, a cooled liquid is recovered which can be recycled to the gas phase and/or to the boiling liquid reaction phase. Some or all of the C4 hydrocarbon feed mixture can be added to this liquid.

In order to carry out the polymerization of the isobutene, a catalyst is used which is generally suitable for cationic olefin polymerization, often called a catalyst of cationic type, in the presence, if appropriate, of a cocatalyst. More particularly, the catalyst can be a halogenated boron compound such as boron trifluoride, or an organoaluminium compound, for example of formula $AlRnXn-3$ in which R is an alkyl radical having, for example, from 1 to 10 carbon atoms, X is a chlorine or bromine atom and n is an integral or fractional number ranging from 0 to 3. The cocatalyst can be water, hydrochloric acid, an alkyl halide such as tert-butyl chloride, or else an alcohol, such as ethanol, especially when boron trifluoride is used as catalyst.

The polymerization reaction can in particular be carried out using an alkyl halide such as tert-butyl chloride as cocatalyst by the process disclosed in European Patent Application EP-A-0 645 402, in combination with ethyldichloroaluminium as catalyst.

The molar ratio of the amount of cocatalyst to the amount of catalyst which are introduced into the reactor is advantageously held at a constant value over time and is between 0.05 and 20, preferably between 1 and 10.

The catalyst and the cocatalyst are preferably introduced into the reactor separately from one another. One of them can be introduced in the C4 hydrocarbon feed mixture. Some or all of the cocatalyst or of the catalyst can be introduced into the reactor in a mixture with another liquid, for example with a portion of the boiling liquid reaction phase which is withdrawn and recycled, which makes it possible to ensure agitation of the reaction medium.

The polymerization reaction can be carried out at a temperature of between $-30$ and $+50°$ C., preferably between $-20$ and $+25°$ C. The absolute pressure of the reactor is a function of the polymerization temperature and can range from 0.03 to 1, preferably from 0.05 to 0.5, MPa. The partial pressure $piC4$ of the isobutene in the gas phase of the reactor can be greater than or equal to $1*10-4$ and less than 1 MPa, preferably greater than or equal to $3*10-4$ and less than 0.5 MPa.

The polymerization temperature is preferably held constant by acting on a cooling fluid of the reactor or of a condenser which is positioned on a line for recycling the gas phase which escapes from the top part of the reactor. Maintaining the temperature constant allows to obtain a product output with a steady concentration of unsaturated terminations.

The process according to the present invention may also comprise a centralized control unit which makes it possible to control the various polymerization parameters, such as the polymerization temperature, the total pressure and the partial pressures in the gas phase of the reactor, the concentration of the various products in the boiling liquid reaction phase, the rates of introduction of the various feeds of the reactor and of withdrawal from the boiling liquid reaction phase, and also the quality of the polyisobutene produced. This centralized control unit may comprise calculation modules and also regulators. A regulator is defined as a system enabling a measured value to be compared with a target value while acting on a physical parameter which makes it possible to change over time the said measured value so as to approach the said target value, taking into account the difference between these two values. The principal inputs of a regulator can therefore be distinguished as being the measured value of the physical parameter and the set point of the said parameter, which can be entered directly into the regulator as a target value by an operator or else displayed as a result of a calculation carried out by a calculation module.

The various process control operations carried out by a centralized control unit, in particular by a regulator, can be carried out directly by an operator.

According to the invention, the partial pressure of isobutene $piC4$ can be the result of a calculation based on the mass concentration of isobutene in the gas phase of the reactor and on the relative or absolute total pressure of the reactor, in particular the product of the absolute or relative total pressure of the reactor with the mass concentration of isobutene in the gas phase. The measured value M of the partial pressure of isobutene $piC4$ is commonly understood to mean the result of the above mentioned calculation, carried out on the basis of the values measured for the relative or absolute total pressure of the reactor and for the mass concentration of isobutene in the gas phase, carried out for example with the aid of a gas chromatograph. In the same way, the action which consists in measuring the partial pressure of isobutene $piC4$ commonly amounts to measuring the two above values and in carrying out the above calculation.

The total pressure in the reactor is generally not held constant and vary according to disturbances such as the quality of the C4 hydrocarbon feed mixture and/or the height of the boiling liquid reaction phase in the reactor.

According to the invention, an empirical relationship between the property P of the polyisobutene produced and the partial pressure of isobutene $piC4$ in the gas phase of the reactor is established beforehand, preferably independently of the polymerization temperature. In practice, the empirical relationship is established by means of series of prior measurements of the property P and of $piC4$ under given polymerization conditions in the reactor. This empirical relationship can be shown in the form of a table in which each value for viscosity or for average molecular mass of the polyisobutene produced is correlated with the partial pressure of isobutene in the gas phase of the reactor.

The target value V for the partial pressure of isobutene in the gas phase of the reactor can be determined using the empirical relationships set out above, on the basis of a desired value for the property P of the polyisobutene produced and various settings of the physical parameters of the polymerization, such as the catalyst flow rate, cocatalyst flow rate, 1-butene concentration and cis- and/or trans-2-butene concentration. It is also possible to enter the desired value for the property P directly into a calculation module which comprises a model consisting of one or more empirical relationships set out above and which calculates the target value V for the partial pressure of isobutene in the gas phase of the reactor.

According to one aspect of the invention, the partial pressure $piC4$ of isobutene in the gas phase of the reactor is measured and is held constant around a target value V by acting on the flow rate of the catalyst introduced into the reactor. The measured value M for the partial pressure of isobutene in the gas phase of the reactor can be compared with the target value V and the difference $E=V-M$ between these two values can be calculated. As a function of the difference E, it is possible to act on the flow rate $Qc$ of catalyst introduced in order to shift the partial pressure of isobutene in the gas phase of the reactor towards the target value V. If the difference E is negative or less than the negative limit of a predetermined range centred around 0, the flow rate $Qc$ of catalyst can be increased. If the difference E is positive or greater than the positive limit of the said range, the flow rate $Qc$ of catalyst can be reduced. If the difference E is zero or is between the limits of the said range, the flow rate $Qc$ of catalyst can remain unchanged This type of process control can advantageously be implemented by the use of a regulator.

According to another aspect of the invention, the partial pressure of isobutene $piC4$ in the gas phase of the reactor is measured and is held constant around a target value V by acting on the flow rate Qh of the C4 hydrocarbon feed mixture. In this case, the actions on the flow rate Qh are made relative to the difference E in a manner which is exactly the opposite of those described above on the flow rate Qc: therefore, instead of increasing the flow rate Qh, it is reduced, and vice versa.

A simplified form of the process may consist in displaying the target value V as the set point C of a regulator of the partial pressure piC4 of isobutene in the gas phase of the reactor. In this case, the process can comprise the following steps:

(a) an empirical relationship is determined between the partial pressure of isobutene in the gas phase of the reactor and the property P, the desired value of the property P is selected, and the target value V of the partial pressure of isobutene in the gas phase of the reactor, corresponding to the desired value of the property P, is calculated by virtue of the said empirical relationship;

(b) the target value V calculated in (a) is displayed as the set point of a regulator of the partial pressure of isobutene in the gas phase of the reactor;

(c) the regulator compares a measured value M for the partial pressure of isobutene in the gas phase of the reactor with the target value V calculated in (a) and calculates the difference E=V−M between these two values;

(d) as a function of the difference E calculated in (c), the regulator acts on the flow rates Qc and/or Qh so as to shift the partial pressure of isobutene in the gas phase of the reactor towards the target value V. In particular, if the regulator acts on the flow rate Qc, alternatively the difference E is negative or less than the negative limit of a predetermined range centred around zero, in which case the flow rate Qc of catalyst is increased; or the difference E is positive or greater than the positive limit of the said range, in which case the flow rate Qc of catalyst is reduced; or the difference E is zero or is within the limits of the said range, in which case the flow rate Qc of catalyst remains unchanged. Furthermore, if the regulator acts on the flow rate Qh, then the actions on the flow rate Qh are carried out, with respect to the difference E, in a manner which is exactly the opposite of those described above on the flow rate Qc: therefore, the flow rate Qh is reduced instead of being increased, and vice versa An elaborated form of the process can consist in displaying, as the set point C of a regulator of the partial pressure piC4 of isobutene in the gas phase of the reactor, the result of a calculation whose result tends towards the target value V by an iterative variation as a function of time. For example, the iterative variation, as a function of time, of the set point C towards the target value V can be a linear variation over time at a predetermined rate which can vary from 100 to 2000 Pa/h, preferably from 300 to 1500 Pa/h. In this case, the process can comprise the following steps:

(a) an empirical relationship is determined between the partial pressure of isobutene in the gas phase of the reactor and the property P, the desired value of the property P is selected, and the target value V of the partial pressure of isobutene in the gas phase of the reactor, corresponding to the desired value of the property P, is calculated by virtue of the said empirical relationship;

(b) the value to be displayed as set point C of a regulator of the partial pressure of isobutene in gas phase of the reactor, in order to reach the target value V calculated in step (a), is calculated by varying the said set point C iteratively over time with, for example, a linear variation, as a function of time, at a predetermined rate which can vary from 100 to 2000 Pa/h, preferably from 300 to 1500 Pa/h;

(c) the regulator compares a measured value M for the partial pressure of isobutene in the gas phase of the reactor with the set point C of the regulator calculated in (b) and calculates the difference E=C−M between these two values;

(d) as a function of the difference E calculated in (c), the regulator acts on the flow rates Qc and/or Qh so as to shift the partial pressure of isobutene in the gas phase of the reactor towards the set point C. In particular, if the regulator acts on the flow rate Qc, alternatively the difference E is negative or less than the negative limit of a predetermined range centred around zero, in which case the flow rate Qc of catalyst is increased; or the difference E is positive or greater than the positive limit of the said range, in which case the flow rate Qc of catalyst is reduced; or the difference E is zero or is within the limits of the said range, in which case the flow rate Qc of catalyst remains unchanged. Furthermore, if the regulator acts on the flow rate Qh, then the actions on the flow rate Qh are carried out, with respect to the difference E, in a manner which is exactly the opposite of those described above on the flow rate Qc therefore, the flow rate Qh is reduced instead of being increased, and vice versa.

A more elaborated form of the process may also consist in limiting the actions of the regulator of the partial pressure piC4 of isobutene in the gas phase of the reactor such that the regulator enters into action only when the measurement of the said partial pressure of isobutene is outside a predetermined range around the target value V. The range can be not more than ±20%, preferably not more than ±10%, around the target value V. In this case, the process can comprise the following steps:

(a) an empirical relationship is determined between the partial pressure of isobutene in the gas phase of the reactor and the property P, the desired value of the property P is selected, and the target value V of the partial pressure of isobutene in the gas phase of the reactor, corresponding to the desired value of the property P, is calculated by virtue of the said empirical relationship;

(b) the target value V calculated in (a) is displayed as set point C of a regulator of the partial pressure of isobutene in the gas phase of the reactor;

(c) the limits of a range of values for the partial pressure of isobutene in the gas phase of the reactor are determined around the target value V, it being possible for the said limits to be not more than ±20%, preferably not more than ±10%, around the target value V;

(d) the regulator compares a measured value M for the partial pressure of isobutene in the gas phase of the reactor with the said limits of the range as determined in (c);

(e) if the measured value M for the partial pressure of isobutene in the gas phase of the reactor is within the limits of the range as determined in (c), the regulator is deactivated and the flow rates Qc and/or Qh remain unchanged;

(f) if the measured value M for the partial pressure of isobutene in the gas phase of the reactor is outside the limits of the range as determined in (c):

(i) the regulator compares the measured value M for the partial pressure of isobutene in the gas phase of the reactor with the set point C of the regulator, and calculates the difference E=C−M between these two values;

(ii) as a function of the difference E, the regulator acts on the flow rates Qc and/or Qh so as to shift the partial pressure of isobutene in the gas phase of the reactor towards the set point C. In particular, if the regulator acts on the flow rate Qc, either the difference E is negative or less than the negative limit of a predetermined range centred around zero, in which case the flow rate Qc of catalyst is increased; or the difference E is positive or greater than the positive limit of the said range, in which case the flow rate Qc of catalyst is reduced; or the difference E is zero or is within the limits of the said range, in which case the flow rate Qc of catalyst remains unchanged. Furthermore, if the regulator acts on the flow rate Qh, then the actions on the flow rate Qh are carried out, with respect to the difference E, in a manner which is exactly the opposite of those described above on the flow rate Qc: therefore, the flow rate Qh is reduced instead of being increased, and vice versa.

Another more elaborated form of the process is able to combine the improvements set out in the two preceding paragraphs. In this case, the process can comprise the following steps.

(a) an empirical relationship is determined between the partial pressure of isobutene in the gas phase of the reactor and the property P, the desired value of the property P is selected, and the target value V of the partial pressure of isobutene in the gas phase of the reactor, corresponding to the desired value of the property P, is calculated by virtue of the said empirical relationship;

(b) the limits of a range of values for the partial pressure of isobutene in the gas phase of the reactor are determined around the target value V;

(c) the regulator compares a measured value M for the partial pressure of isobutene in the gas phase of the reactor with the limits of the range as determined in (b);

(d) if the measured value M for the partial pressure of isobutene in the gas phase of the reactor is within the limits of the range as determined in (b), the regulator is deactivated and the flow rates Qc and/or Qh remain unchanged;

(e) if the measured value M for the partial pressure of isobutene in the gas phase of the reactor is outside the limits of the range as determined in (b):

(i) the value to be displayed as set point C of a regulator of the partial pressure of isobutene in the gas phase of the reactor is calculated, in order to attain the target value V calculated in step (a), by varying the said set point C iteratively according to, preferably, a linear variation as a function of time and with a predetermined rate;

(ii) the regulator compares the measured value M for the partial pressure of isobutene in the gas phase of the reactor with the set point C of the regulator, and calculates the difference E=C−M between these two values;

(iii) as a function of the difference E, the regulator acts on the flow rates Qc and/or Qh so as to shift the partial pressure of isobutene in the gas phase of the reactor towards the set point C. In particular, if the regulator acts on the flow rate Qc, alternatively the difference E is negative or less than the negative limit of a predetermined range centred around zero, in which case the flow rate Qc of catalyst is increased; or the difference E is positive or greater than the positive limit of the said range, in which case the flow rate Qc of catalyst is reduced; or the difference E is zero or is within the limits of the said range, in which case the flow rate Qc of catalyst remains unchanged. Furthermore, if the regulator acts on the flow rate Qh, then the actions on the flow rate Qh are carried out, with respect to the difference E, in a manner which is exactly the opposite of those described above on the flow rate Qc: therefore, the flow rate Qh is reduced instead of than being increased, and vice versa One variant of the above forms of the process can consist in the regulator acting simultaneously on the flow rate Qc and Qh. As described above, a measured value M for the partial pressure of isobutene in the gas phase of the reactor is compared with the set point C of the regulator and the difference E=C−M between these two values is calculated. As a function of the difference E, the regulator acts simultaneously on the flow rates Qh and Qc so as to shift the partial pressure of isobutene in the gas phase of the reactor towards the set point C: alternatively, the difference E is negative or less than the negative limit of a predetermined range centred around zero, in which case the flow rate Qh is reduced and the flow rate Qc is increased; or the difference E is positive or greater than the positive limit of the said range, in which case the flow rate Qh is increased and the flow rate Qc is reduced; or the difference E is zero or is within the limits of the said range, in which case the flow rates Qh and Qc remain unchanged.

According to one of the preferred embodiments in the present invention, it is found to be more advantageous to keep the partial pressure piC4 constant around the target value V by acting solely on the flow rate Qc of the catalyst introduced.

One of the advantages of the present invention is to improve the stability of the polymerization reaction and to reduce the polydispersity, i.e. the breadth of the distribution of the molecular masses of the polyisobutene produced.

Another advantage of the present invention is to be able to held the polymerization temperature constant with another process control, independent of the process control according to the present invention that is used to maintain the viscosity or the average molecular weight of the polymer produced at a constant desired value. Hence, by maintaining constant the temperature independently of the viscosity or the average molecular weight allows to obtain a polymer with a steady quality and with a constant insaturated termination content.

FIG. 1 shows diagrammatically an apparatus for producing polyisobutene by continuous polymerization of isobutene in a reactor (1) which essentially comprises a cylindrical part (2). The reactor comprises a boiling liquid reaction phase (3) and a gas phase (4) which is above and in equilibrium with the said liquid phase. The reactor is equipped with a feed pipe for a C4 hydrocarbon feed mixture (5) comprising the monomer, with a catalyst feed pipe (6) and, optionally, with a cocatalyst feed pipe (7), the said pipes emerging in the cylindrical part (2) containing the boiling liquid reaction phase (3). The bottom part of the reactor is equipped with a pipe (8) for withdrawing the boiling liquid reaction phase which leads towards a purification device (9) comprising, for example, at least one distillation column, which column is intended for isolating the polymer produced via a pipe (10). The top part of the reactor containing the gas phase (4) can be equipped with a line (11), for recycling the gas phase, on which line is mounted a condenser (12) which allows the gas phase to be cooled and condensed by means of a cooling fluid which circulates in a pipe (13), the resultant condensate being returned into the reactor (1). In the top part of the reactor containing the gas phase, a manometer (14) allows the total pressure in the reactor to be measured, and an analyser (15), such as a gas chromatograph, allowing the mass concentration of isobutene in the gas phase to be measured. These two instruments are connected to a centralized control unit (16) whose elements, such as regulators and calculation modules, are described diagrammatically in FIG. 2.

Figure 2:
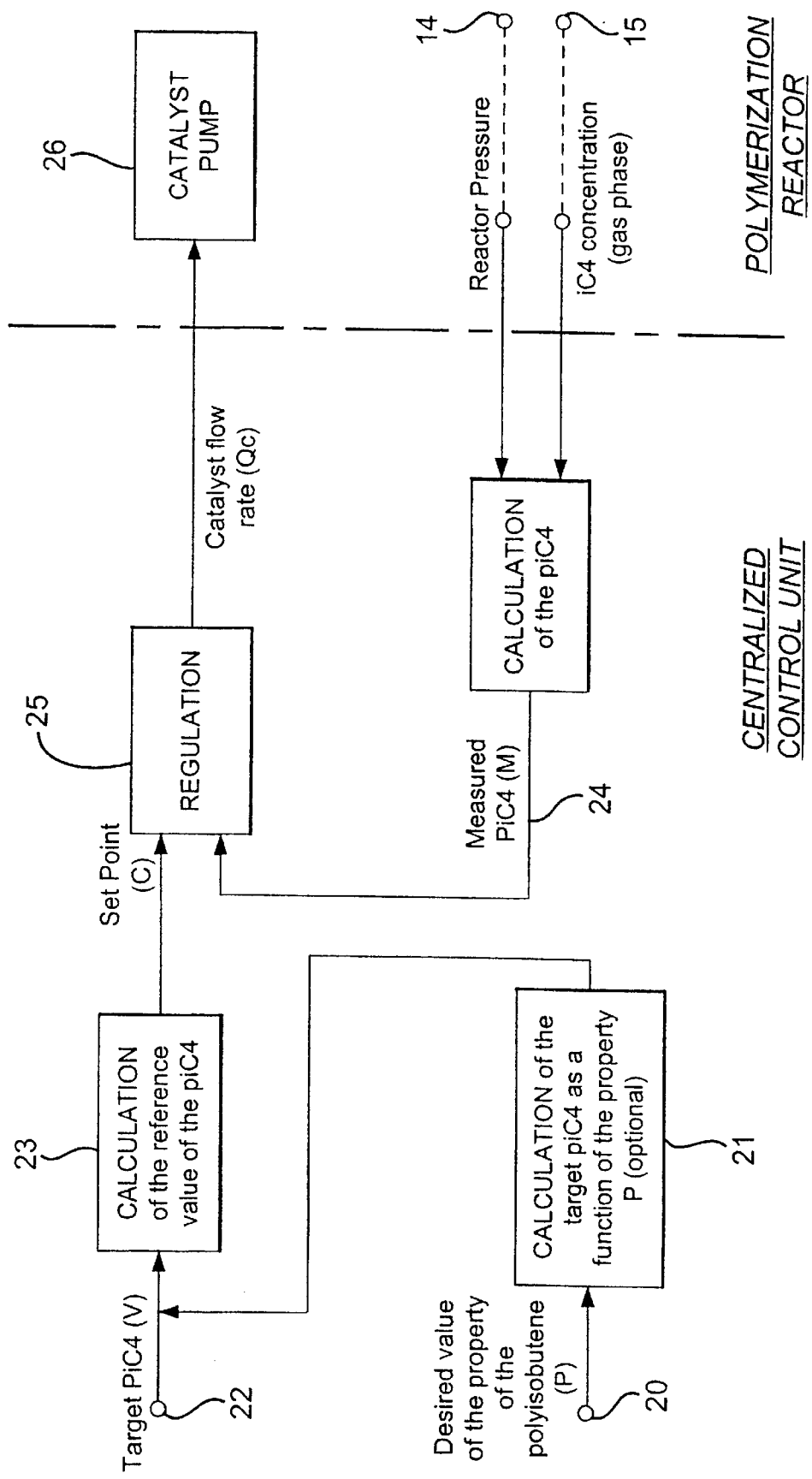
FIG. 2 shows, by way of example, a schematic diagram for controlling the property P of the polyisobutene produced continuously in accordance with the present invention.

FIG. 2 shows by way of example a schematic diagram of the process control according to the process of the present invention. For the elements described in the invention, this diagram shows on one side the instrumentation and equipment of the polymerization reactor (POLYMERIZATION REACTOR) and on the other side a functional schematic of the process control, which can be integrated into a centralized control unit (CENTRALIZED CONTROL UNIT).

According to FIG. 2, a calculation module (21) makes it possible to calculate the target value V for the partial pressure of isobutene piC4 in the gas phase of the reactor on the basis of the desired value (20) of the property P of the polyisobutene, by using an empirical relationship established beforehand between the property P of the polyisobutene produced and the partial pressure piC4 of the isobutene in the gas phase of the reactor. The target value V (22) can, however, be calculated and entered directly by an operator into a calculation module (23). This module (23) makes it possible to calculate the set point C of the partial pressure piC4 of the isobutene in the gas phase of the reactor on the basis of the target value V, by varying the said set point C iteratively over time. Another calculation module (24) is used to calculate the partial pressure piC4 of the isobutene in the gas phase of the reactor on the basis of the measurement of the relative or absolute total pressure of the reactor, carried out for example using the manometer (14), and of the measurement of the mass concentration of isobutene in the gas phase, carried out for example using the analyser (15), such as a gas chromatograph. The module (24) therefore yields a measured value M for piC4 which is transmitted to a regulator (25). This regulator (25):

(i) compares the measured value M of piC4 with the set point C calculated by the calculation module (23) and calculates the difference E=C−M between these two values;

(ii) as a function of the difference E, the regulator (25) acts, for example, on the flow rate Qc of catalyst delivered by a pump (26) in order to shift the partial pressure piC4 towards the set point C: alternatively, the difference E is negative or less than the negative limit of a predetermined range centred around zero, in which case the flow rate Qc of catalyst is increased; or the difference E is positive or greater than the positive limit of the said range, in which case the flow rate Qc of catalyst is reduced; or the difference E is zero or is within the limits of the said range, in which case the flow rate Qc of catalyst remains unchanged.

Figure 3:
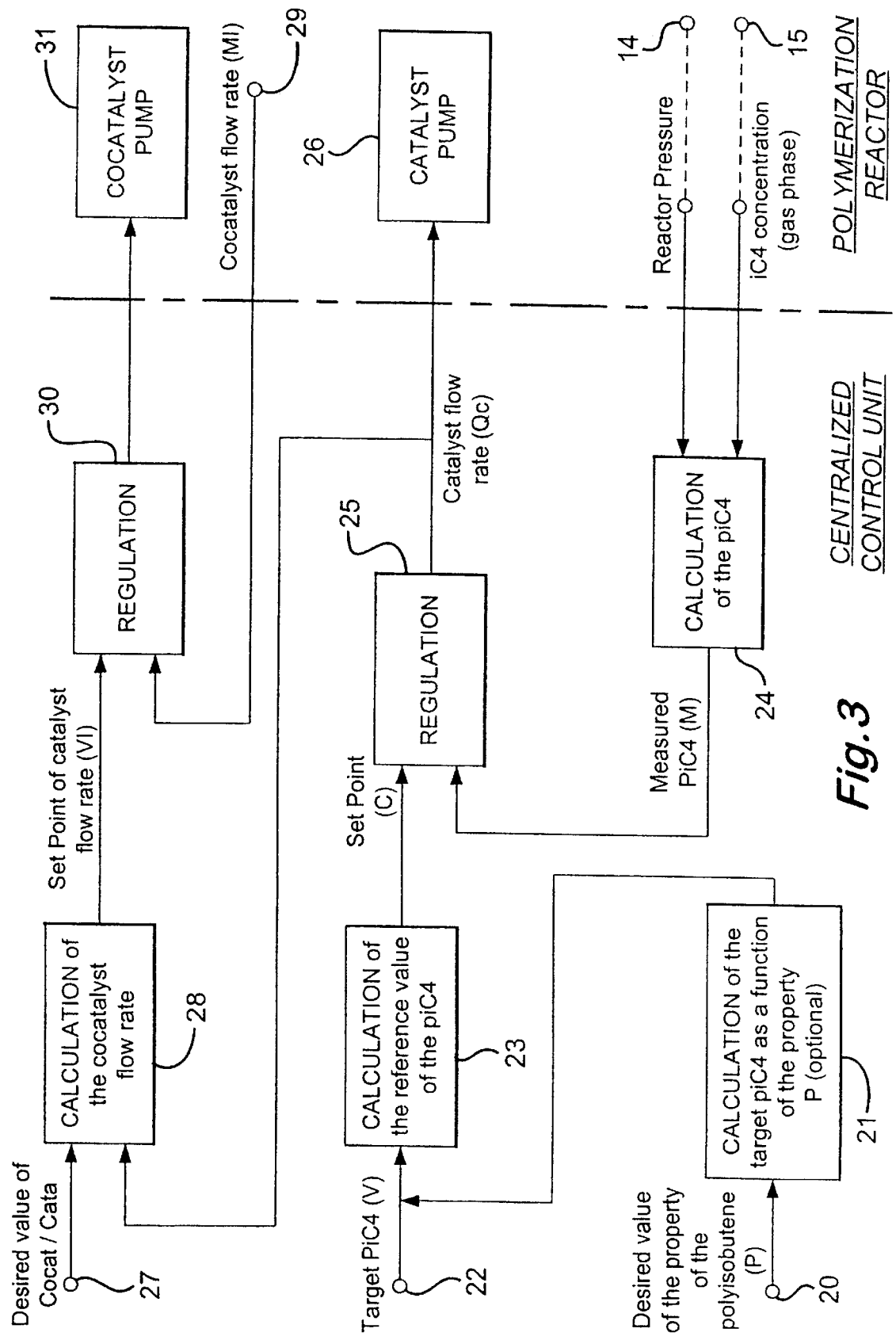
FIG. 3 shows, by way of example, a schematic diagram for controlling, which is improved relative to that shown in FIG. 2.

A preferred variant of the present invention is shown diagrammatically in FIG. 3, which in particular uses the elements labelled identically to those of FIG. 2. Furthermore, a catalyst and a cocatalyst are used simultaneously, the molar ratio of the amounts thereof introduced into the reactor being maintained at a constant desired value. Thus, in addition to the elements shown in FIG. 2, the diagram comprises a calculation module (28) which makes it possible, on the basis of the value for the flow rate of catalyst Qc calculated by the regulator (25), to calculate a desired value V1 for the flow rate of cocatalyst to be introduced into the reactor in order to maintain the molar ratio of the quantity of cocatalyst to the quantity of catalyst introduced at a constant desired value (27) which is entered by an operator into the calculation module (28). A regulator (30)

(i) compares a measured value M1 (29) for the flow rate of cocatalyst introduced into the reactor with the value V1 for the flow rate of cocatalyst calculated by the calculation module (28) and calculates the difference E1=V1−M1 between these two values;

(ii) as a function of the difference E1, the regulator (30) acts on the flow rate of cocatalyst delivered by a pump (31) into the reactor in order to shift the flow rate of cocatalyst towards the desired value V1 calculated by the calculation module (28)

EXAMPLE 1

A device for continuous polymerization of isobutene as shown schematically in FIG. 1 was employed, including a reactor (1) consisting of a cylindrical part (2).

This reactor was fed continuously with a C4 hydrocarbon feed mixture through the conduit (5) containing by weight, 31% of 1-butene, 7% of cis 2-butene, 7% of trans 2-butene, 48% of isobutene and 7% of butanes. The total flow rate of the liquid C4 hydrocarbon feed mixture was 14.21 T/h.

The polymerization temperature was 10° C.; the total absolute pressure in the reactor was 0.132 MPa. The catalyst system included tert-butyl chloride as cocatalyst and ethyldichloroaluminium as catalyst. The catalyst and the cocatalyst were introduced continuously through the feed pipes respectively (6) and (7) with flow rate respectively of 5.86 kg/h and 4.72 kg/h.

Figure 4:
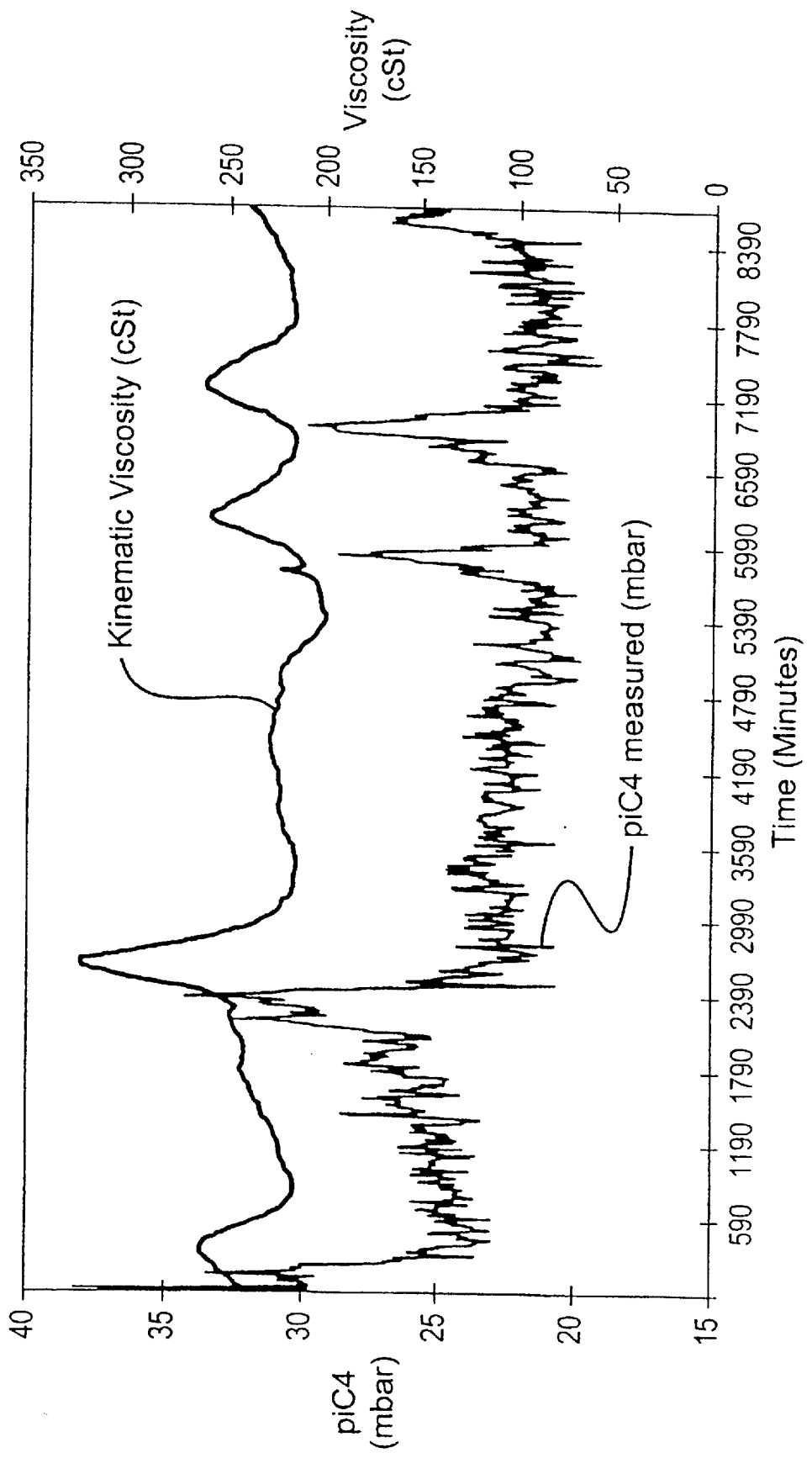
FIG. 4 shows, by way of Example 1, a graphic representing over time, piC4 measured and the kinematic viscosity of the polybutene produced.

The trends represented in FIG. 4 showed the variation of the partial pressure of isobutene, piC4, measured in the gas phase of the reactor (1) and the kinematic viscosity as a function of time for a period of 6 days. Surprisingly, it was observed that the kinematic viscosity of the polyisobutene produced followed approximately the same trend than piC4 with a delay corresponding to the residence time of the polyisobutene downstream the reactor prior to kinematic viscosity analysis. It appears clearly that piC4 was an image of the kinematic viscosity of the polyisobutene after its purification. Hence, an empirical relation was set between the kinematic viscosity of the polyisobutene produced and piC4. A process control was built on the principle of maintaining the kinematic viscosity of the polyisobutene produced constant around a desired value, where piC4 is held constant at the relevant value corresponding to the kinematic viscosity desired value.

EXAMPLE 2

The conditions were identical to those of Example 1 except that the C4 hydrocarbon feed mixture contained by weight, 24% of 1-butene, 10% of cis 2-butene, 9% of trans 2-butene, 51% of isobutene and 6% of butanes, the total flow rate of the liquid C4 hydrocarbon feed mixture was 14.67 T/h; the reaction temperature was 10° C.; the total absolute pressure in the reactor was 0.121 NPa. The flow rate of catalyst was varying between 14 and 18.6 kg/h and the flow rate of cocatalyst was varying between 3.5 to 4.9 kg/h The process according to the present invention was used.

Figure 5:
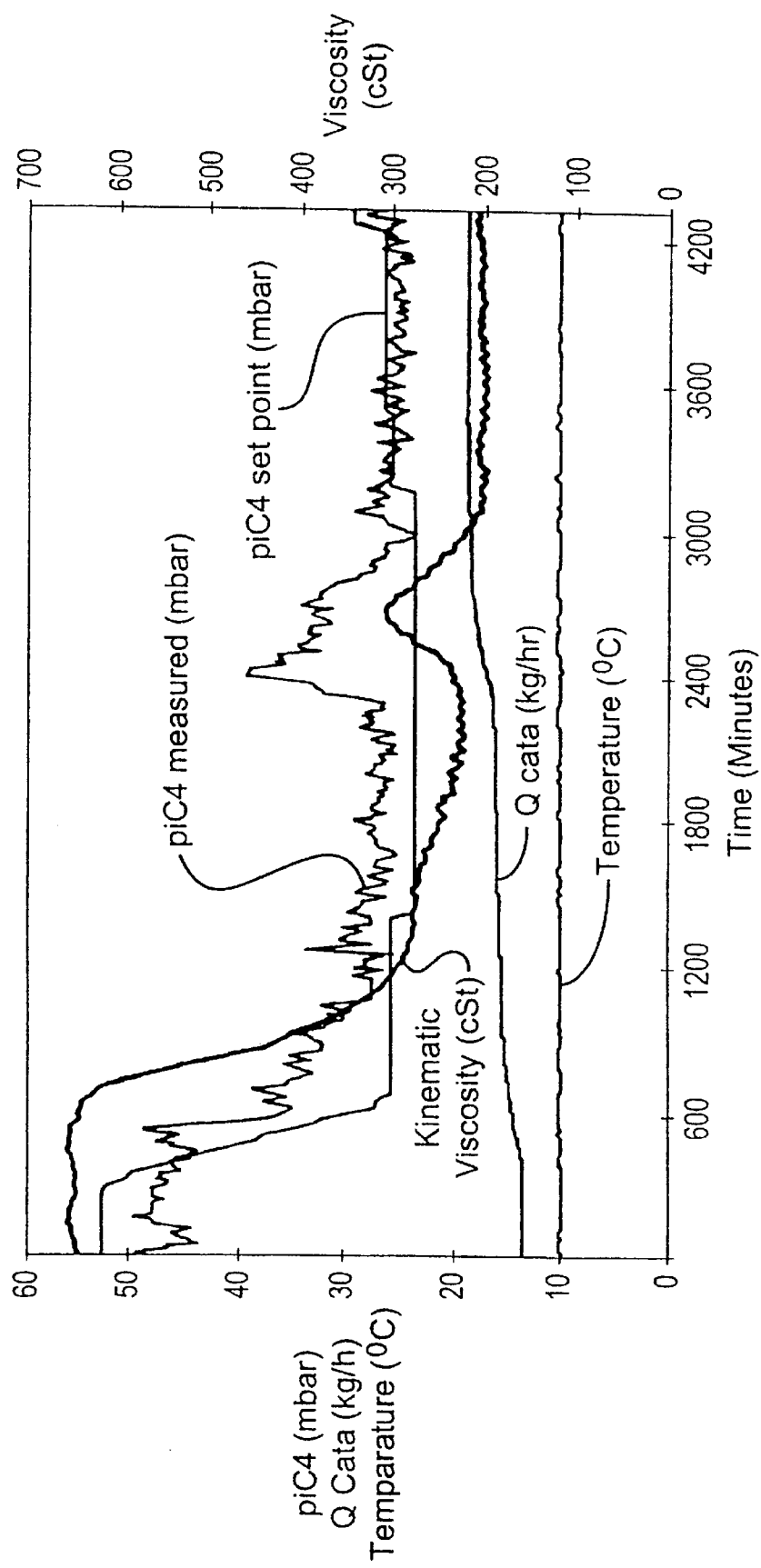
FIG. 5 shows, by way of Example 2, a graphic representing over time various parameters such as, the polymerization temperature, the set point and the measured value of piC4, the flow rate of catalyst and the kinematic viscosity of the polyisobutene produced.

The trends represented in FIG. 5 showed the polymerization temperature (referred as "Temperature" in FIG. 5) maintained constant, and, the set point and the measured value of the partial pressure of isobutene, piC4, and the kinematic viscosity of the polyisobutene as a function of time for a period of three days of the polyisobutene production. On the same graphic, the flow rate of catalyst (referred as "Q Cata" in FIG. 5) was also represented and varying twice during the three days of production.

The measured value of piC4 followed, as expected, the variation of the set point which was changed several times during the three days. The set point of piC4 was changed step by step in order to set the kinematic viscosity of the polyisobutene at the desired value.

During the period up to approximately 2300 minutes, the kinematic viscosity was reduced from 600 cSt down to 200 cSt by setting piC4 accordingly and the process control automatically increased the flow rate of catalyst. After 2300 minutes the measured value of piC4 suddenly raised, in spite of the unchanged piC4 set point. This event was probably caused by the presence of impurities in the C4 hydrocarbon feed mixture. At the meantime the catalyst flow rate automatically raised in order to compensate the effect of the impurities and to bring back the measured pic4 to its set point value. After approximately 3000 minutes, the piC4 set point was finally tuned step by step in order to obtain the desired kinematic viscosity.

What is claimed is:

1. Process for maintaining a property P of a polyisobutene at a constant desired value in the course of an isobutene polymerization conducted continuously in a reactor comprising a boiling liquid reaction phase which contains the monomer and the polymer being formed and is in equilibrium with a gas phase on top of the said liquid phase, the process comprising:

conducting the polymerization by continuous introduction into the reactor of a catalyst and of a C4 hydrocarbon feed mixture comprising the monomer;

continuously withdrawing from the reactor the liquid reaction phase; and subsequently subjecting the liquid reaction phase continuously to at least one purification step which is intended to isolate the polyisobutene produced;

wherein the property P is selected from the group consisting of viscosity and the average molecular mass of the polyisobutene produced; and wherein, by virtue of an empirical relationship established beforehand between the property P of the polyisobutene produced and the partial pressure piC4 of the isobutene in the gas phase of the reactor, a target value V is determined for piC4, corresponding to the desired value of the property P; and wherein, during the polymerization, the partial pressure piC4 in the gas phase of the reactor is measured and the said partial pressure piC4 is held constant at around the said target value V by acting on the flow rate Qc of the catalyst introduced into the reactor and/or on the flow rate Qh of the C4 hydrocarbon feed mixture.

2. Process according to claim 1, wherein the property P is selected from the group consisting of the kinematic viscosity, the specific viscosity, the reduced viscosity and the intrinsic viscosity of the polyisobutene produced.

3. Process according to claim 1, wherein the property P is selected from the group consisting of the number-average molecular mass Mn, the weight-average molecular mass Mw and the viscometric average molecular mass Mv of the polyisobutene produced.

4. Process according to claim 1, wherein a catalyst is used which is suitable for cationic polymerization in the presence of a cocatalyst and wherein the molar ratio of the amount of cocatalyst to the amount of catalyst which are introduced into the reactor is held at a constant value.

5. Process according to claim 4, wherein the molar ratio of the amount of cocatalyst to the amount of catalyst which are introduced into the reactor is between 0.05 and 20.

6. Process according to claim 5, wherein the molar ratio of the amount of cocatalyst to the amount of catalyst which are introduced into the reactor is between 1 and 10.

7. Process according to claim 1, comprising the following steps:

(a) determining an empirical relationship between the partial pressure piC4 of isobutene in the gas phase of the reactor and the property P, selecting the desired value of the property P, and calculating the target value V of piC4, corresponding to the desired value of the property P, by virtue of the said empirical relationship;

(b) displaying the target value V calculated in step (a) as the set point of a regulator of the partial pressure piC4 of isobutene in the gas phase of the reactor;

(c) causing the regulator to compare a measured value M for the partial pressure piC4 of isobutene in the gas phase of the reactor with the target value V calculated in step (a) and calculating the difference $E=V-M$ between these two values;

(d) causing the regulator, as a function of the difference E calculated in step (c), to act on the flow rates Qc and/or Qh so as to shift the partial pressure piC4 of isobutene in the gas phase of the reactor towards the target value V.

8. Process according to claim 1, wherein the target value V of piC4 is reached by an iterative variation as a function of time of the said partial pressure piC4 of isobutene and wherein the process comprises the following steps:

(a) determining an empirical relationship between the partial pressure piC4 of isobutene in the gas phase of the reactor and the property P, selecting the desired value of the property P, and calculating the target value V piC4, corresponding to the desired value of the property P, by virtue of the said empirical relationship;

(b) calculating the value to be displayed as set point C of a regulator of the partial pressure piC4 of isobutene in the gas phase of the reactor, in order to reach the target value V calculated in step (a), by varying the said set point C iteratively over time;

(c) causing the regulator to compare a measured value M for the partial pressure piC4 of isobutene in the gas phase of the reactor with the set point C of the regulator calculated in step (b) and calculating the difference $E=C-M$ between these two values;

(d) causing the regulator, as a function of the difference E calculated in step (c), to act on the flow rates Qc and/or Qh so as to shift the partial pressure piC4 of isobutene in the gas phase of the reactor towards the set point C.

9. Process according to claim 8, wherein the target value V of piC4 is reached by an iterative variation, which is linear as a function of time, of the said partial pressure piC4 of isobutene with a rate varying from 100 to 2000 Pa/h.

10. Process according to claim 8, wherein the target value V of piC4 is reached by an iterative variation, which is linear as a function of time, of the said partial pressure piC4 of isobutene with a rate varying from 500 to 1500 Pa/h.

11. Process according to claim 1, wherein a regulator of the partial pressure piC4 of isobutene in the gas phase of the reactor enters into action only when the measurement of the said partial pressure of isobutene is outside a predetermined range around the target value V and in that the process comprises the following steps:

(a) determining an empirical relationship between the partial pressure piC4 of isobutene in the gas phase of the reactor and the property P, selecting the desired value of the property P, and calculating the target value V of piC4, corresponding to the desired value of the property P, by virtue of the said empirical relationship;

(b) displaying the target value V calculated in step (a) as set point C of a regulator of the partial pressure piC4 of isobutene in the gas phase of the reactor;

(c) determining the limits of a range of values for the partial pressure piC4 of isobutene in the gas phase of the reactor around the target value V;

(d) causing the regulator to compare a measured value M for the partial pressure piC4 of isobutene in the gas phase of the reactor with the said limits of the range as calculated in step (c);

(e) if the measured value M for the partial pressure piC4 of isobutene in the gas phase of the reactor is within the limits of the range as determined in step (c), the regulator is deactivated and the flow rates Qc and/or Qh remain unchanged;

(f) if the measured value M for the partial pressure piC4 of isobutene in the gas phase of the reactor is outside the limits of the range as determined in step (C):

(i) the regulator compares a measured value M for the partial pressure piC4 of isobutene in the gas phase of the reactor with the set point C of the regulator, and calculates the difference E=C−M between these two values;

(ii) as a function of the difference E, the regulator acts on the flow rates Qc and/or Qh so as to shift the partial pressure piC4 of isobutene in the gas phase of the reactor towards the set point C.

12. Process according to claim 11, wherein the predetermined range the target value V is not more than ±20% around V.

13. Process according to claim 11, wherein the predetermined range around the target value V is not more than ±10% around V.

* * * * *